United States Patent [19]

Fischetti

[11] 4,160,826
[45] Jul. 10, 1979

[54] INHIBITOR PREPARATION FOR THE ABSORPTION OF LIPIDS, BASED ON DIETHYLAMINOETHYLDEXTRAN

[75] Inventor: Ignazio Fischetti, Rome, Italy

[73] Assignee: Laboratory Biochimici Fargal-Pharmasint S.p.A., Pomezia, Italy

[21] Appl. No.: 743,425

[22] Filed: Nov. 19, 1976

[30] Foreign Application Priority Data

Dec. 12, 1975 [IT] Italy ................. 52661 A/75

[51] Int. Cl.$^2$ ..................... A61K 31/73; C08B 37/02
[52] U.S. Cl. ........................ 424/180; 536/51; 536/112

[58] Field of Search ................ 424/180; 536/51, 112

[56] References Cited

U.S. PATENT DOCUMENTS 3,629,230  12/1971  Soderqvist ............... 536/51
3,851,057  11/1974  Kuzuya ................... 536/51

Primary Examiner—Johnnie R. Brown
Attorney, Agent, or Firm—Pollock, Vande Sande & Priddy

[57] ABSTRACT

Pharmacological preparation having an inhibiting action on the lipids absorption, wherein it contains, as active agent, diethylaminoethyldextran.

5 Claims, 3 Drawing Figures

Fig. 3
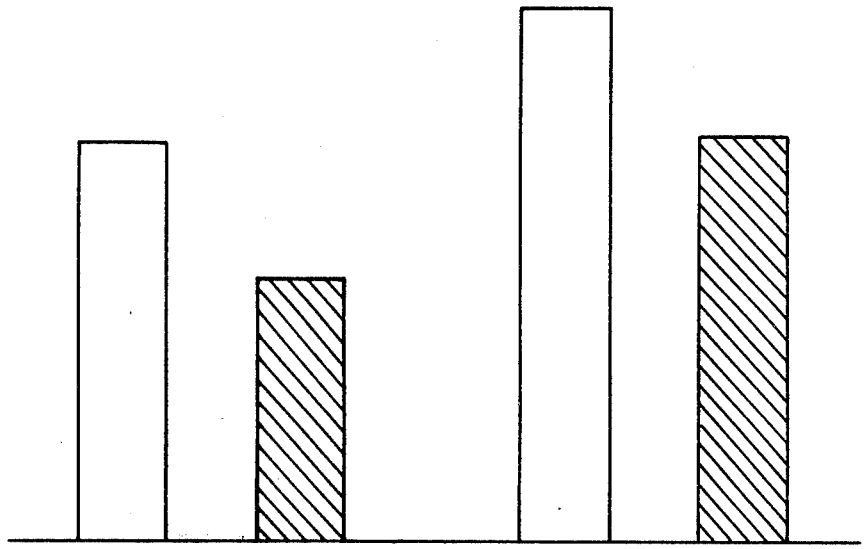
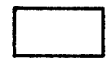

INHIBITOR PREPARATION FOR THE ABSORPTION OF LIPIDS, BASED ON DIETHYLAMINOETHYLDEXTRAN

BACKGROUND OF INVENTION

The object of the present invention is an inhibitor preparation for the absorption of lipids, based on diethylaminoethyldextran. In particular the present invention relates to a pharmacological preparation of the aforesaid type having an antisteatogenous- and hypolipidemizing action, which allows the control of undesirable increases in body weight.

The inconveniences deriving from fat accumulation in the human body organs, in particular in the liver, as well as the discomfort and the dangers caused by an overincrease in the body weight in subjects either submitted to a hyperlipidic- or to a normal diet, are well know. Moreover, the increase beyond safety limits, of some hematic parameters such as lipemia, triglycerids and cholesteremia, as it is well known, causes in the human organism, conditions predisposing to circulatory- and arteriosclerotic affections.

The advantage, therefore, of a pharmaceutical preparation which allows the control in a unitary and efficacious way of the accumulation of lipids in the human body and of the related consequences of this accumulation at an organic and hematic level, is evident.

SUMMARY OF INVENTION

This combined action is assured by the object of the present invention, a diethylaminoethyldextran based preparation, indicated from here on as DEAE-D.

In fact it has been discovered surprisingly that DEAE-D, if administered in the proper doses, indicated hereinafter, produces the aforesaid inhibiting action on the lipids absorption at organic and hematic level.

DESCRIPTION OF PREFERRED EMBODIMENTS

Figure 1:
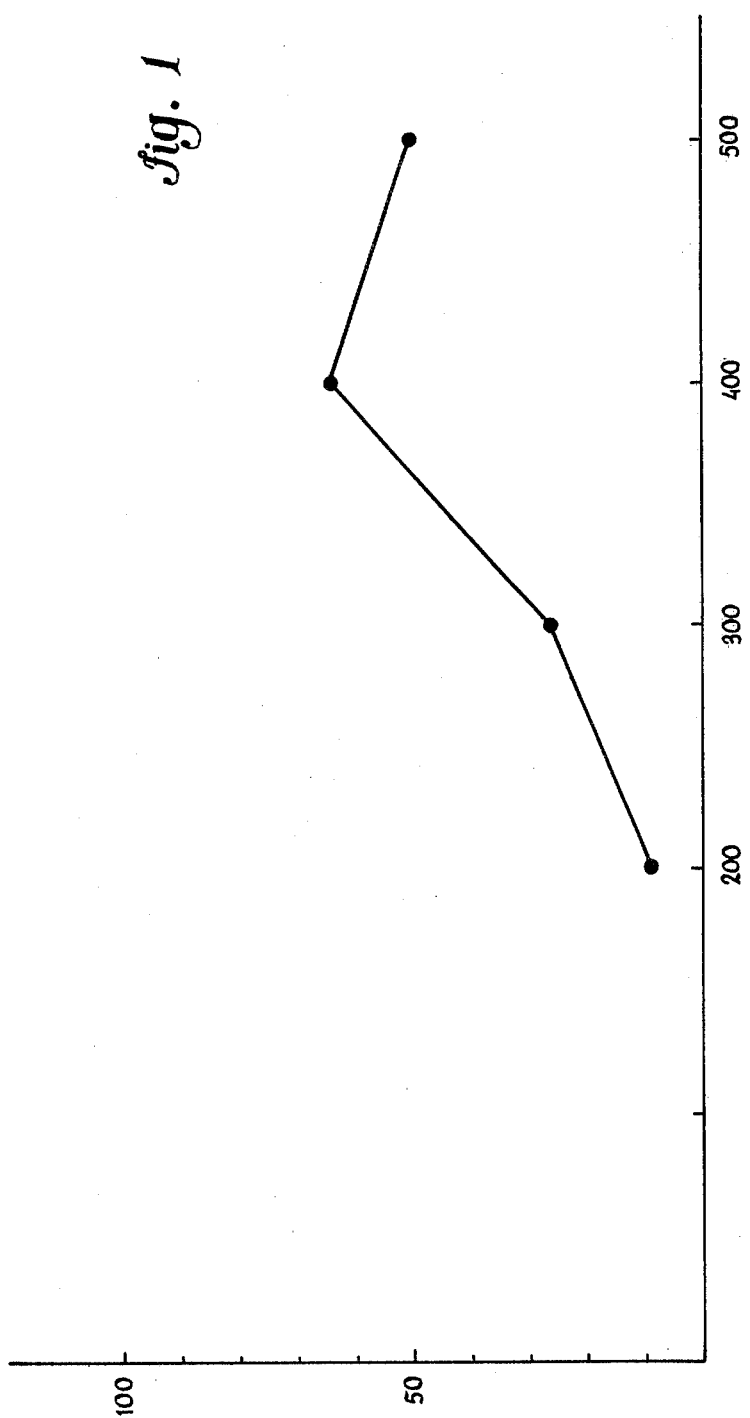

The diethylaminoethyldextran (DEAE-D), which constitutes an active principle of the preparation of the present invention, was already known in the industrial field, but for completely different uses, that is as a stimulating agent for the cellular absorption of the nucleic acids and proteins. There are, instead, no indications of any kind of products based on DEAE-D used for the purposes of the present invention.

In order to summarize how, according to the present invention, the DEAE-D has been identified as an agent inhibitor of the absorption of lipids, it is desirable to keep in mind the following considerations:

The diethylaminoethyldextran is a derivative of dextran presenting remarkable polyelectrolyte characteristics. It is known that macromolecules containing a high number of ionizable residues of the same type, because of electrostatic effects, interact easily with substances having an opposite charge, with a consequent sequestering of these latter substances by the polyelectrolyte. This process, for example, is exploited on chromatography on ionic exchange resins, which consist of an insoluble matrix to which anionic or cationic groups are linked. The interaction of the counterion with the polyelectrolyte depends, naturally, besides on the nature of the ionizable groups on the two substances, on the pH and on the ionic strength of the solvent.

In the case of DEAE-D the thought occurred of exploiting its polyelectrolyte properties in order to attempt to interfere, at a gastro-intestinal level, on the digestion and absorption processes of the fats and, indirectly, on their metabolism. The DEAE-D is a hydrosoluble derivative of dextran containing a large amount of diethylaminoethyl groups.

This product, which has an average molecular weight and a molecular weight distribution similar to the original dextran, (variable therefore according to polymerization degree), interferes with the fat digestion- and re-absorption mechanism. In fact, under the pH- and ionic strength conditions prevailing at intestinal level, the DEAE-D, a rather strong polycation, has a tendency to bind stably substances having a decidedly acid character, such as the fatty acids and the bile acids. Consequently, an inhibition of the digestion- and of the absorption of lipids occurs with different mechanisms: from one side the sequestering of the bile acids hinders the emulsification of the neutral fats and the activation of the pancreatic lipases; on the other side the interaction of the polyelectrolyte with the fatty acids deriving from the hydrolysis of the neutral fats, hinders both their absorption and their activating action of the lipase. Because of the DEAE-D action, even a decrease of the endogenous cholesterol by indirect mechanism has been evidenced. In fact, the sequestering of the bile acids hinders their entero-hepatic circulation and therefore, ends in stimulating their neosynthesis originating from cholesterol.

Therefore, the DEAE-D offers unquestionable advantages of efficaciousness and tolerance as compared to other polyelectrolytes and, above all, to the insoluble ones.

The fact of being soluble, renders it certainly more active also on the mechanic phase, so far as its sequestering action is concerned; besides, the macromolecular matrix to which the diethylaminoethyl groups are bound is the dextran, a well known polysaccharide already used in therapy (for example, as a plasma substitute), devoid of toxicity and whose metabolism is well known.

From what has been said hereinabove, the definition of a product based on DEAE-D, which satisfies the request of a combined action with regard to the accumulation of lipids at the organic- and hematic level, according to the present invention, has been attained.

Therefore, it is a special object of the present invention, a pharmacological preparation having an inhibiting action on the absorption of the lipids at a body organic- and hematic level, characterized by the fact of containing, as active component, diethylaminoethyldextran (DEAE-D).

The doses for a correct use of the preparation of the present invention are those comprised in the interval from 2 to 4 g of DEAE-D per day.

With regard to the toxicity and the tolerance of the DEAE-D at the indicated doses the following has to be observed:

(A) the DEAE-D has to be considered in practice as devoid of acute toxicity. In fact it is unable to cause cases of death, or any immediate or belated toxic symptomatology if administered to the rat orally in doses up to 5000 mg/kg and endoperitoneally in doses up to 100 mg/kg.

(B) The DEAE-D in experiments of prolonged oral administration to the growing rat, has presented remarkably good general and local tolerance. By daily administrations and for up to 60 consecutive days it has not caused: (a) death cases; (b) modifications of some important biochemical hematic constants and of the hepatic chromosecretory function; (c) modification in the weight of the principal organs, nor the appearance of neoplasias; (d) tropic alterations of the gastroenteric mucose.

(C) The DEAE-D has attained in the rat fed with Handler steatocirrhogenic diet an intense and dose-dependent antisteatogenic activity.

(D) The DEAE-D proved to be devoid of side effects on the arterial pressure and on the respiration of the narcotized rat.

Conclusively, the remarkable antisteatogenic activity of DEAE-D suggests its use in the human clinic in all those cases wherein it is desired to limit its reabsorption. The toxicological- and general tolerance characteristics are such as to warrant a wide margin of safety with respect to damaging side actions or, anyway, with undesirable actions for administration in doses from 2 to 4 g per day.

The present invention will be described now with particular reference to practical examples of use of the product based on DEAE-D, at the above indicated doses, in cases of different affections due to lipids accumulation.

EXAMPLE 1

Antagonistic action on hepatic steatosis in the Handler steato-cirrhogenic diet

The antisteatogenic activity of DEAE-D has been evaluated on the hepatic steatosis caused in the rat, by the Handler steatocirrhogenic diet.

Said diet corresponds to the following composition and has been supplied by the firm Drs Piccioni of Brescia:

| | |
|---|---|
| -course casein | 10% |
| -saccharose | 59% |
| -cotton seed oil | 10% |
| -lard | 15% |
| -cod liver oil | 2.5% |
| -Osborne and Mendel saline mixture | 3% |
| -cholesterol | 0.5% |
| -vitaminic integration, cholin excluded | + |

The search has been performed on albino Wistar rats of both sexes whose weight is specified in the following Table (I).

DEAE-D doses of 200–300–400 and 500 mg/kg have been tested. For each dose a distinct group of experiments has been performed, so that the action of each dose has been evaluated in comparison with the results obtained with its own control group (this in order to make more superimposable the extraction conditions of the hepatic lipids).

In particular, for each dose, a group of animals has been fed with Handler diet for a period of no less than 24 days, while another group has been fed with the same diet and, in addition, has received orally the established dose of DEAE-D. This dose has been solubilized in distilled water in the proper way, so that the desired amount could be administered in a volume of 10 ml/kg by means of an esophageal probe. The blanks received at the same time 10 ml/kg of tap water always by esophageal probe. The administration was performed in the first hours of the morning. A group of 10 rats has been fed with normal diet (MIL) in pellets) and after 25 days of treatment with tap water 10 ml/kg/die/os it has been killed in order to perform the hepatic lipids extraction.

Results are reported in detail in the subsequent Table (I). They allow to drive the following considerations:

(1) The Handler steatocirrhogenic diet under the experimental conditions, stops generally the bodily increase of the rat in the range of the 25 days of treatment.

(2) In comparison with the blanks under normal diet, a sharp increase in the total hepatic lipids contents is observed. This last, in fact, goes from an average of 37 mg/g in the rats under normal diet to an average of 106–160 mg/g in the rats under steatocirrhogenic diet, with an increase, therefore, of three-four times as much.

(3) The weight of the liver also is increased in a remarkable way.

The DEAE-D treatment inhibits in a significant way the increase of hepatic lipids caused by the steatocirrhogenic diet. The antisteatosic action has to be considered as dose-dependent. In fact, for the 200–300 and 400 mg/kg doses of DEAE-D, there exists a highly positive correlation (r=+0.9913); the straight line is represented by the following equation:

$$y = 48.63 + 0.278X^{(*)}$$

(*) L. Cavalli-Sforza, Statistical Analysis for physicians and biologists; Boringhieri Ed., Turin 1961, pp. 87–95.

The $ED_{50}$ thus calculated proved to be equal to 355 mg/kg.

The 400- and 500 mg/kg doses produce in practice an effect of maximal type, as under the experimental conditions, the lowering of the hepatic lipids content below 55–60 mg/g was impossible.

The histochemical tests also have confirmed the antisteatogenic effect of DEAE-D.

Paralleling the inhibition of the hepatic lipids accumulation, the weight of the liver, increased by the diet, is reduced and brought back within normal limits by the DEAE-D treatment.

These results are illustrated in the diagram of FIG. 1 wherein is indicated in ordinates the inhibition % dose-dependent on the Handler diet hepatic steatosis in the rat by the DEAE-D, as a function of increasing values of the dose expressed as mg/kg on the abscissae.

Table I

Antagonistic action of DEAE-D on the hepatic steatosis caused by Handler diet on the Wistar rat of both sexes

| An. no. | Group | and sex | 25 consecutive days treatment per os | Initial weight g | Final weight g | Liver weight in mg/100 g body weight | Total hepatic lipids in mg/100 g of fresh liver |
|---|---|---|---|---|---|---|---|
| 10 | A | ♂ | Blanks under normal diet | 118 ± 9.7 | 229.8 ± 16.46 | 3,968 ± 70.9 | 36.9 ± 2.45 |
| 8 | B | ♀ | Handler diet | 157 ± 7 | 179.7 ± 8.5 | 4,718 ± 220 | 105.7 ± 30.2 (=100) |
| 8 | B₁ | ♀ | Handler diet + DEAE-D 200 mg/kg | 145 ± 3.5 | 164.0 ± 5.6 | 4,133 ± 190 | 95.3 ± 17.5 (−9,1%) |

Table I-Continued
Antagonistic action of DEAE-D on the hepatic steatosis caused by Handler diet on the Wistar rat of both sexes

| An. no. | Group | and sex | 25 consecutive days treatment per os | Initial weight g | Final weight g | Liver weight in mg/100 g body weight | Total hepatic lipids in mg/100 g of fresh liver |
|---|---|---|---|---|---|---|---|
| 7 | C | ♂ | 175.5 ± | 197.7 ± 1.48 | 4,630 ± 7.2 | 116.1 ± 14.31 95.1 | P>0.5 (=100) |
| 8 | C₁ | ♂ | Handler diet + DEAE-D 300 mg/kg | 224.5 ± 5.4 | 218.8 ± 9.5 | 3,397 ± 151 | 85.6 ± 9.1 (−27.3%) P 0.1−0.05 |
| 8 | D | ♂ | Handler diet | 262 ± 6.5 | 263 ± 8.5 | 4,331 ± 63 | 160.0 ± 8.83 (=100) |
| 5 | D₁ | ♂ | Handler diet + DEAE-D 400 mg/kg | 267 ± 8.1 | 258 ± 11 | 3,396 ± 800 | 56.4 ± 13.42 (−64.7%) P<0.01 |
| 6 | E | ♂ | Handler diet | 305 ± 9.5 | 295.3 ± 11.8 | 4,187 ± 201 | 115.3 ± 17.5 (=100) |
| 7 | E₁ | ♂ | Handler diet + DEAE-D 500 mg/kg | 264 ± 6.2 | 261.2 ± 5.7 | 3,910 ± 134 | 57.1 ± 8.36 (−50.5%) P 0.02−0.01 |

EXAMPLE 2

Antagonistic action on hepatic steatosis and on hyperlipidemia on Nath and Coll (*) hypercholesterolic diet These tests have been performed on male Wistar rats on Nath and Coll hypercholesterolic diet (1959)*.
(*) Nath, N.A., Harper, E. and Elvhjem, C.A., J. Nutrit., 67, 239, (1959).

Tests have been performed on 4 groups of 8 randomly selected rats which have been treated in the following way:

group a: blanks under normal diet;
group b: hypercholesterolic diet;
group c: hypercholesterolic diet + DEAE-D 350 mg/kg/day by esophageal probe.
group d: hypercholesterolic diet + DEAE-D 350 mg/kgX2/day, always by esophageal probe.

The treatment lasted 21 days.

The DEAE-D in group d has been administered in the first hours of the morning and in the late afternoon. In group c in the first hours of the morning. The chosen dose is equal to the ED$_{50}$ active in an antisteatogenic sense (Handler diet).

At the end of the pre-established treatment period the animals have been killed by means of decapitation.

The total lipids by the Zollner and Kirsch method (1962) and the total cholesterolemia (Huan and coll., 1961) have been determined on the blood collected from the trunk.

The DEAE-D at the 350 mg/kg/day single dose does not modify in a significant way the liver weight as well as the total hepatic lipids, the total hematic lipids as well as the cholesterolemia, with respect to the blanks on hypercholesterol diet. On the contrary, when the same dose of DEAE-D is repeated twice in the same day one observes a reduction of the weight of the liver at the limits of the statistical significance, a significant reduction of 35% of the total hepatic lipids, a 22% significant reduction of lipidemia, while the 17.3% reduction of cholesterolemia does not reach the statistical significance.

These data confirm the remarkable hepatic antisteatosic action of DEAE-D and they disclose that it performs a hypolipidemizing- but not a hypocholesterolemizing action.

The treatment lasted 60 days. The body weight has been measured every day at the moment of the treatment in the rats of group c and in those of the other two experimental groups and recorded at regular intervals. Also, the general condition of all the rats has been followed.

Results

Figure 2:
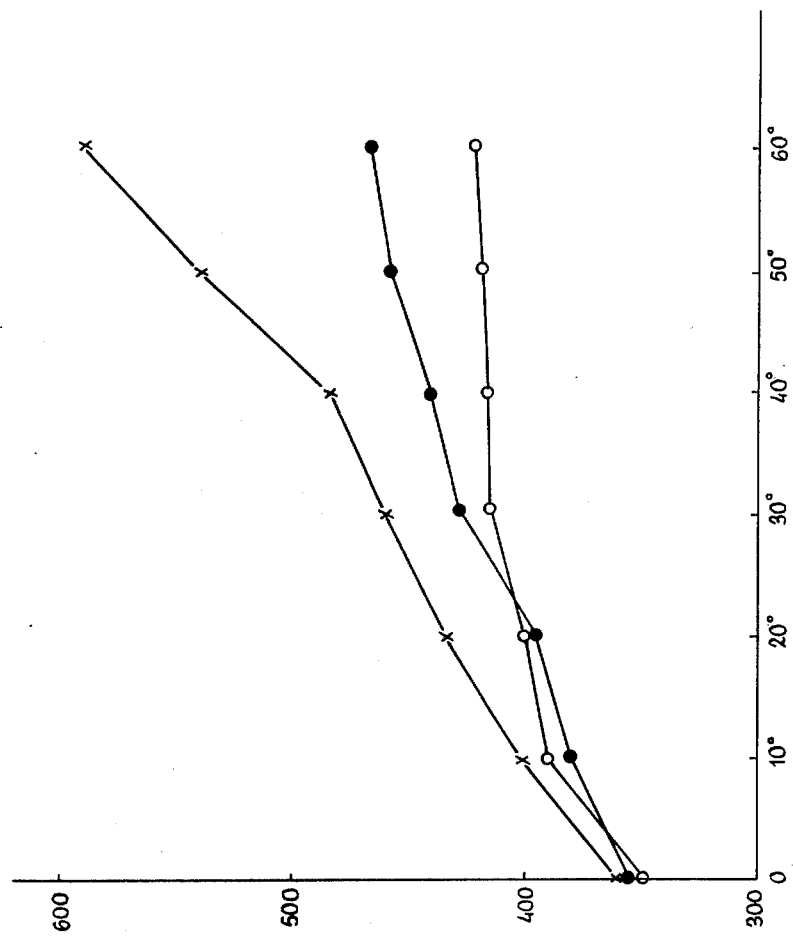

The results related to the body weight are reported in detail in FIG. 2 inherent to the antagonistic action of DEAE-D on the obesities of the rat on the Balboriak lipogenic diet, wherein on the ordinates the body weight in grams, and on the abscissae the day of the treatment are reported. It can be seen thus, that the treatment inhibits almost completely the increase in body weight produced in the rat by the Balboriak lipogenic diet.

EXAMPLE 3

Effect of the DEAE-D administration on body weight of subjects with ponderal excess under normal diet 30 patients ranging from 41 to 84 years old, of which 15 males and as many females, have been chosen.

All of them presented a ponderal excess with respect to the values of the normal subject, calculated by the Lorentz formula:

$$P = A - 100(A - 150/4)$$

wherein P represents the weight of the normal subject and A the height of the subject.

The treatment has been extended for a period varying between ten and sixteen days. The posology used has been of two grams of DEAE-DEXTRAN per day, administered in two doses, at eight AM and at four PM, one gram each time. 0.500 g capsules of DEAE-D have been used.

The following parameters have been controlled on the patients before and after the treatment:

Urine analysis;

Azotemia;
Glycemia;
Hemochromocytometric test;
Transaminase;
Triglyceridemia;
Cholesterolemia;
Body weight.

The appearance of side effects besides, has been evaluated in each single patient.

The following Tables II and III report the ponderal variations singly obtained in the fifteen male patients and in the fifteen female patients. It should be remembered that all patients have been treated while they were hospitalized and that normocaloric diets which were not far removed from those habitually followed by the patients at their home have been adopted, and, anyway, such as to repress in every case the feeling of hunger.

| Patient | Treatment days | BODY WEIGHT Before with ponderal excess | | After | |
|---|---|---|---|---|---|
| (1) G.V. | 10 | 70 | (+9) | 67 | (+6) |
| (2) D.M.M. | 10 | 142 | (+77) | 126 | (+61) |
| (3) P.C. | 11 | 66 | (+10) | 64 | (+8) |
| (4) B.A. | 10 | 60 | (+2.5) | 50 | (0.5) |
| (5) F.G. | 10 | 61 | (+4.5) | 58 | (1.5) |
| (6) P.M. | 10 | 72 | (+11) | 66 | (+5) |
| (7) F.P. | 10 | 65 | (+9) | 61 | (+5) |
| (8) D.P.B. | 8 | 58 | (+8) | 53 | (+3) |
| (9) S.F. | 10 | 72 | (9) | 68 | (+5) |
| (10) D.A. | 11 | 69 | (+9) | 67 | (+7) |
| (11) D.P.G. | 10 | 73 | (+6.5) | 69 | (+2.5) |
| (12) P.A. | 10 | 59 | (+4) | 58 | (+3) |
| (13) C.A. | 10 | 61 | (+6) | 57 | (°2) |
| (14) C.B. | 12 | 68 | (+10.5) | 64 | (+6.5) |
| (15) M.A. | 10 | 72 | (+16) | 67 | (+11) |

TABLE III

| Patient | Treatment days | BODY WEIGHT Before with ponderal excess | | After | |
|---|---|---|---|---|---|
| (1) C.A. | 26 | 68 | (16.5) | 62.8 | (11) |
| (2) Z.F. | 21 | 90 | (30) | 84 | (24) |
| (3) G.A. | 15 | 76 | (24.5) | 73.5 | (22.5) |
| (4) M.A. | 11 | 78 | (21) | 70 | (13) |
| (5) P.I. | 11 | 74 | (8.5) | 70 | (4.5) |
| (6) C.R. | 11 | 72 | (9) | 67 | (4) |
| (7) M.R. | 9 | 104 | (46.5) | 96 | (38.5) |
| (8) M.G. | 8 | 74 | (15) | 70 | (11) |
| (9) M.T. | 12 | 74 | (20) | 70 | (15.5) |
| (10) M.C. | 16 | 77 | (28.5) | 73 | (24.5) |
| (11) C.T. | 17 | 75 | (11.5) | 72.5 | (9) |
| (12) P.M. | 13 | 50 | (15) | 46 | (−2.5) |
| (13) P.T. | 14 | 54 | (5.5) | 50 | (3.5) |
| (14) P.C. | 12 | 80 | (16.5) | 79 | (15.5) |
| (15) G.M. | 13 | 64 | (4) | 61.9 | (1.9) |

Laboratory tests performed before and after the treatment have shown no significant variations, a fact which points out the non-toxicity of the product under examination. The clinical examination of the patients, performed daily, has not evidenced undesirable side effects in any case, neither general nor local symptoms of intolerance have been shown.

The weight control shows a ponderal decrement in all the examined patients.

It has been ascertained that in the group of fifteen men (wherein before the treatment there was an average ponderal excess of 12.8 kg), a weight reduction equal in average to 4 kg per capita has been verified.

The women who presented an average ponderal excess of 17.2 kg, have undergone an average reduction of 4,200 kg per capita, as it can be seen in the diagram of FIG. 3.

EXAMPLE 4

Effect of the administration of DEAE-Dextran on the body weight and on the hematic parameters of subjects submitted to a hypercaloric diet No. 16 subjects, ranging from 13 to 43 years old, carrying on normal work activity and free from clinically demonstrable illness, with weight excess have been submitted to a diet of above 3000 cal/day. The results allow the underscoring of the perfect tolerance of the pharmaceutical product which was administered in doses of 2 g, twice a day, for a total of four g.

The hematic data regarding lipemia, the triglycerids, the cholesterolemia, the ratio B/alpha lipoproteic and the body weight have been taken into consideration 20 days after the therapy.

From the examination of the results it has been evidenced an average ponderal reduction equal to 7.1 kg within the 20th day. Equally appreciable has been the reduction of the average lipemic values which from 875.7 mg/100 ml was reduced to 647 mg/100 ml, as well as for the values of triglycerids and cholesterol which went from 177.3 mg/100 ml to 139.8 mg/100 ml and from 327.6 mg/100 ml to 188.4 mg/100 ml, respectively. The B/alpha lipoproteic ratio has been reduced from 3.6 to 2.8, a significantly statistic notion.

In another study group, 5 subjects having a sedentary type of activity submitted to a hypercaloric diet have been examined. This group was compared with an analogous group of patients (No. 7 subjects, ranging from 17 to 20 years old) which was following the same type of diet in addition to the pharmacological product (administration of 2 g, three times a day, at the meals).

The data of the first of the two groups (only diet), permitted the observance of a rapid ponderal increase within the 20th day (averaging + 3 kg), while the lipemia values went from 531 mg/100 ml to 768 mg/100 ml, the cholesterol values, from 176 mg/100 ml to 188 mg/100 ml, and those of the triglycerids from 106 mg/100 ml to 119 mg/100 ml. On the contrary the B/alpha lipoproteic ratio was scarcely modified.

The second group (diet + pharmacological product) followed also for 20 days, showed a stabilization of the weight with minor modifications from 67.8 to 68.5 kg, not statistically significant.

The lipemia values, on the contrary, showed a sharp reduction (from 685 mg/100 ml to 611 mg/100 ml), as well as the cholesterolemia values (from 202 mg/100 ml to 197 mg/100 ml). Scarcely modified were the data inherent to triglyceridemia which did not result appreciably modified at the 20th day. On the contrary the value of the lipoproteic ratio showed a sharp and significant reduction (from 2.0 to 1.8).

In particular the lipemia was reduced to an average value of 606 mg/100 ml, while the values of the cholesterolemia (187 mg/100 ml) and of triglycerids (97 mg/100 ml) appeared also to be reduced.

As a comparison No. 20 subjects, ranging from 20 to 26 years old, with normal working activity and submitted to an analogous hypercaloric diet, have been taken under examination; the variations related to cholesterol, triglycerids, B/alpha-lipemia and body weight were also followed within such a group at the 20th day of hyperalimentation.

The values related to the weight have shown an increase equal to 3 kg, likewise the cholesterolemia has shown positive variations from 241 mg/100 ml to 262 mg/100 ml as well as the lipemia (from 812 mg/100 ml to 852 mg/100 ml) and the triglyceridemia (126 mg/100 to 139 mg/100 ml).

Finally the B/alpha lipoproteic ratio has shown significant statistical variations (from 3.4 to 3.7).

Finally No. 10 subjects, ranging from 18 to 32 years old, having normal working activity, have been submitted to a hypocaloric diet (800 calories). The variations related to cholesterol, triglycerids, lipidemia, B/alpha lipoproteic ratio and body weight have been checked within a period (ambulatorily).

In this group of patients an average ponderal modification, going from 94.7 to 91.7 kg has been, while the triglycerids and the cholesterol changed from 148 mg/100 ml to 140 mg/100 ml and from 215 mg/100 ml to 204 mg/100 ml, respectively.

The lipemia showed analogous variations (from 825 mg/100 ml to 779 mg/100 ml) while the B/alpha lipoproteic ratio has not been modified (3.3).

From the examination of the results, there is no doubt about the DEAE-D activity which has produced significant variations of the hematic values in both the groups treated, however, the average ponderal values in the sedentary subjects have been contained within positive oscillations which appear to be minimal if compared with the same values concerning the non-treated subject having normal working activity.

Particularly significant are the data resulting from treated subjects on a hypercaloric diet and with normal working activity in comparison with non-treated subjects on a hypocaloric diet, wherein both the average body weight and the hematic values show variations less favourable than those observed in subjects treated with DEAE-Dextran and on a hypercaloric diet.

The present invention has been described with particular reference to its specific embodiments, but it must be understood that variations or modifications may be introduced without thereby departing from the scope of the present invention.

Having thus described the present invention, what is claimed is:

1. A process of treating subjects having excess weight for obtaining both antisteatogenous action and a reduction in weight which comprises administering a pharmacological preparation consisting essentially of diethylaminoethyl dextran as active agent and a pharmaceutical carrier wherein the diethylaminoethyl dextran is administered in doses of 1 to 2 grams twice a day for a total of 2 to 4 grams per day.

2. The process of claim 1 wherein said carrier is water.

3. The process of claim 1 wherein the diethylaminoethyl dextran is administered to subjects under normal diet in doses of 1 gram twice a day for a total of 2 grams per day.

4. The process of claim 1 wherein the diethylaminoethyl dextran is administered to subjects under hypercaloric diet in doses of 2 grams twice a day for a total of 4 grams per day.

5. A pharmacological preparation for obtaining antisteatogenic action and reduction of the body weight of a subject consisting of diethylaminoethyl dextran dissolved in distilled water wherein the amount of said dextran is such that doses of 1 to 2 grams twice a day for a total of 2 to 4 grams per day can be administered to a subject.

* * * * *